US010000727B2

(12) United States Patent
Sodd

(10) Patent No.: US 10,000,727 B2
(45) Date of Patent: Jun. 19, 2018

(54) PACKAGED COMPOSITION

(71) Applicant: The Procter & Gamble Company, Cincinnati, OH (US)

(72) Inventor: Vincent Sodd, Mentor, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 359 days.

(21) Appl. No.: 14/532,513

(22) Filed: Nov. 4, 2014

(65) Prior Publication Data

US 2016/0122693 A1 May 5, 2016

(51) Int. Cl.

*A61L 9/04* (2006.01)
*A61K 8/00* (2006.01)
*C11D 3/50* (2006.01)
*C11D 3/37* (2006.01)
*C11D 17/06* (2006.01)
*C11D 17/04* (2006.01)

(52) U.S. Cl.

CPC .............. *C11D 3/50* (2013.01); *C11D 3/3707* (2013.01); *C11D 3/505* (2013.01); *C11D 17/041* (2013.01); *C11D 17/06* (2013.01)

(58) Field of Classification Search

CPC .......... C11D 3/50; C11D 3/3707; C11D 17/06
USPC .......................................................... 512/4, 1
See application file for complete search history.

(56) References Cited

U.S. PATENT DOCUMENTS 4,279,579 A 7/1981 Froeschke
5,013,498 A 5/1991 Froeschke
5,770,235 A 6/1998 Baumann et al.
7,867,968 B1 * 1/2011 Aouad ..................... C08K 7/22 510/296
8,476,219 B2 * 7/2013 Aouad ................ C11D 3/3707 512/4
2012/0270765 A1 10/2012 Aouad
2015/0143278 A1 * 5/2015 Hawkins ............... G06F 3/0236 715/773

FOREIGN PATENT DOCUMENTS

WO 2010/119065 * 10/2010

OTHER PUBLICATIONS

U.S. Appl. No. 14/532,497, filed Nov. 4, 2014, Sodd et al.
International Search Report for International Application Serial No. PCT/US2015/058710, dated Jan. 27, 2016, 9 pages.

* cited by examiner

*Primary Examiner* — Jessica Whiteley
(74) *Attorney, Agent, or Firm* — Gary J. Foose

(57) ABSTRACT

A packaged composition including a plurality of particles in a package, wherein the particles include: more than about 40% by weight of the particles of polyethylene glycol, wherein the polyethylene glycol has a weight average molecular weight from about 5000 to about 11000; and from about 0.1% to about 20% by weight of the particles of perfume; wherein substantially all of the particles in the package have a substantially flat base and a height measured orthogonal to the base and together the particles have a distribution of heights, wherein the distribution of heights has a mean height between about 1 mm and about 5 mm and a height standard deviation less than about 0.3.

20 Claims, 10 Drawing Sheets

PACKAGED COMPOSITION

FIELD OF THE INVENTION

Packaged composition.

BACKGROUND OF THE INVENTION

Particulate laundry scent additives are commonly employed by consumers to enhance their scent experience with doing laundry and using laundered articles subsequent to washing. Typically, particulate laundry scent additives are marketed in opaque packages to protect the particles from photo-degradation.

Some particulate laundry scent additives are not so sensitive to exposure to light, particularly laundry scent additives that reside in the product supply chain for only a short duration. For such laundry scent additives, it can be advantageous to the marketer to be able to show the consumer the particles at the point of product selection on a shelf in a store. This is often accomplished by using a clear package or a package having a clear portion. For some product packages, the fill level of the particulate laundry scent additive is visible at the point of product selection or when the product is used by the consumer, for instance by opening the package.

Particulate laundry scent additives are commonly sold in a quantity based on weight. Depending on the quality of the manufacture of the particulate laundry scent additive, the particles may have a wide variety of sizes within a single package or across several packages. Such variability in particle size of particulate laundry scent additives can result in packages containing the same mass having different fill levels within the package. This can generate consternation among consumers who may incorrectly conclude that a package having the lowest fill level contains less product than a package having a higher fill level. This can also raise other regulatory concerns related to slack fill in containers.

With these limitations in mind, there is a continuing unaddressed need for a particulate laundry scent additive that can be filled in packages on a weight basis that provide for a relatively uniform fill level amongst different packages.

SUMMARY OF THE INVENTION

A packaged composition comprising a plurality of particles in a package, wherein the particles comprise: more than about 40% by weight of the particles of polyethylene glycol, wherein the polyethylene glycol has a weight average molecular weight from about 5000 to about 11000; and from about 0.1% to about 20% by weight of the particles of perfume; wherein substantially all of the particles in the package have a substantially flat base and a height measured orthogonal to the base and together the particles have a distribution of heights, wherein the distribution of heights has a mean height between about 1 mm and about 5 mm and a height standard deviation less than about 0.3.

DETAILED DESCRIPTION OF THE INVENTION

Figure 1:
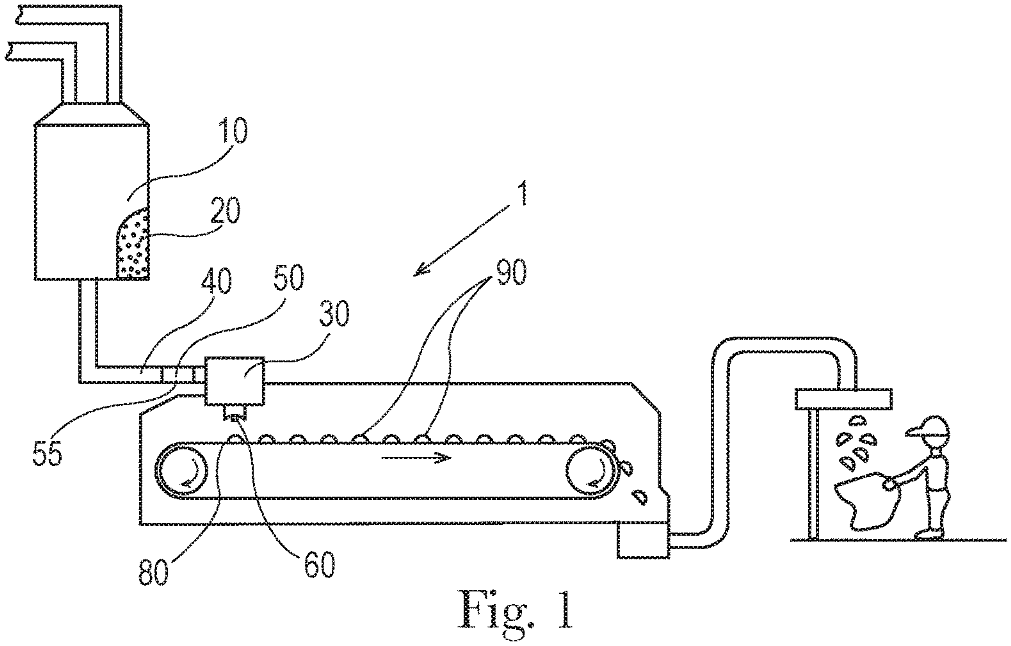
FIG. 1 is an apparatus for forming particles.

An apparatus 1 for forming particles is shown in FIG. 1. The raw material or raw materials are provided to a batch mixer 10. The batch mixer 10 has sufficient capacity to retain the volume of raw materials provided thereto for a sufficient residence time to permit the desired level of mixing and or reaction of the raw materials. The material leaving the batch mixer 10 is the precursor material 20. The precursor material 20 can be a molten product. The batch mixer 10 can be a dynamic mixer. A dynamic mixer is a mixer to which energy is applied to mix the contents in the mixer. The batch mixer 10 can comprise one or more impellers to mix the contents in the batch mixer 10.

Between the batch mixer 10 and the distributor 30, the precursor material 20 can be transported through the feed pipe 40. The feed pipe 40 can be in fluid communication with the batch mixer 10. An intermediate mixer 55 can be provided in fluid communication with the feed pipe 40 between the batch mixer 10 and the distributor 30. The intermediate mixer 55 can be a static mixer 50 in fluid communication with the feed pipe 40 between the batch mixer 10 and the distributor 30. The intermediate mixer 55, which can be a static mixer 50, can be downstream of the batch mixer 10. Stated otherwise, the batch mixer 10 can be upstream of the intermediate mixer 55 or static mixer 55 if employed. The intermediate mixer 55 can be a static mixer 50. The intermediate mixer 55 can be a rotor-stator mixer. The intermediate mixer 55 can be a colloid mill. The intermediate mixer 55 can be a driven in-line fluid disperser. The intermediate mixer 55 can be an Ultra Turrax disperser, Dispax-reactor disperser, Colloid Mil MK, or Cone Mill MKO, available from IKA, Wilmington, N.C., United States of America. The intermediate mixer 55 can be a perforated disc mill, toothed colloid mill, or DIL Inline Homogenizer, available from FrymaKoruma, Rheinfelden, Switzerland.

The distributor 30 can be provided with a plurality of apertures 60. The precursor material 20 can be passed through the apertures 60. After passing through the apertures 60, the precursor material 20 can be deposited on a moving conveyor 80 that is provided beneath the distributor 30. The conveyor 80 can be moveable in translation relative to the distributor 30.

The precursor material 20 can be cooled on the moving conveyor 80 to form a plurality of solid particles 90. The cooling can be provided by ambient cooling. Optionally the cooling can be provided by spraying the under-side of the conveyor 80 with ambient temperature water or chilled water.

Once the particles 90 are sufficiently coherent, the particles 90 can be transferred from the conveyor 80 to processing equipment downstream of the conveyor 80 for further processing and or packaging.

The intermediate mixer 55 can be a static mixer 50. The static mixer 50 can be mounted in fluid communication with the feed pipe 40. A static mixer 50 provides for transport of the precursor material 20 through the static mixer 40 and one or more obstructions within the static mixer 50 that disrupts flow of the precursor material 20 through the static mixer 50. The disruption of flow of the precursor material 20 within the static mixer mixes the precursor material 20. The energy required for mixing the precursor material 20 as it flows through the static mixer is derived from the loss in energy of the precursor material 20 as it flows through the static mixer. A static mixer 50 is a mixer in which the energy required for mixing is derived from the loss in energy of the material passing through the static mixer 50.

Figure 2:
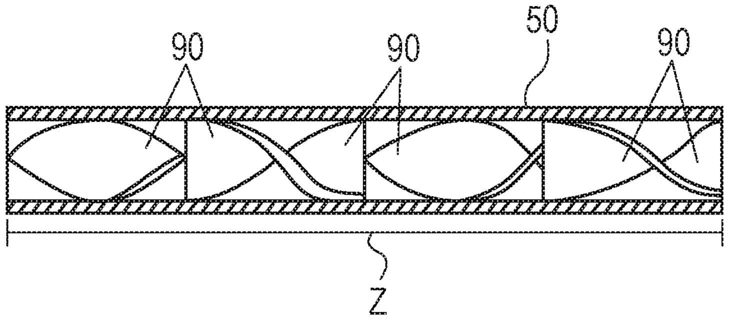
FIG. 2 is helical static mixer.
Figure 3:
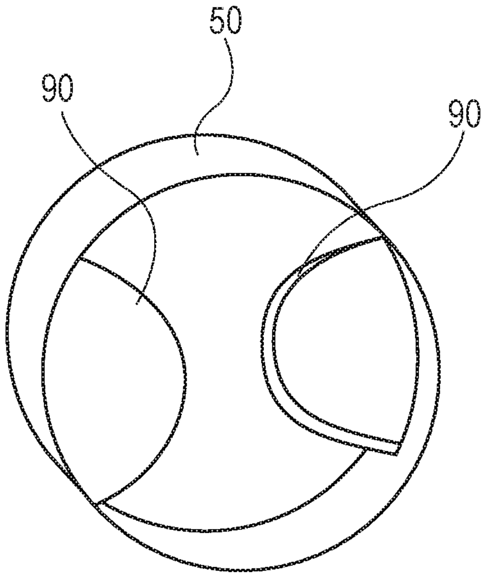
FIG. 3 is a plate type static mixer.

There are a variety of static mixers 40 that can be employed in the apparatus 1. The static mixer 50 can be a helical static mixer 40 as shown in FIG. 2. As shown in FIG. 2, a helical static mixer 50 can comprise one or more fluid disrupting elements 90. Optionally, the static mixer 50 can be a plate static mixer 50 as shown in FIG. 3 comprising one or more fluid disrupting elements 90. The static mixer 50 can be provided in a cylindrical or squared housing or other suitably shaped housing. A variety of different arrangements of fluid disrupting elements 90 can be provided. The fluid disrupting elements 90 can be designed to split the flow of the precursor material 20 into multiple streams and direct those streams to various positions across the cross section of the static mixer. The fluid disrupting elements 90 can be designed to provide for turbulence in the flow of the precursor material 20, the eddies created by the turbulence mixing the precursor material 20. The static mixer 50 can be a Kenics 1.905 cm inside diameter KMS 6, available from Chemineer, Dayton, Ohio, USA.

Figure 4:
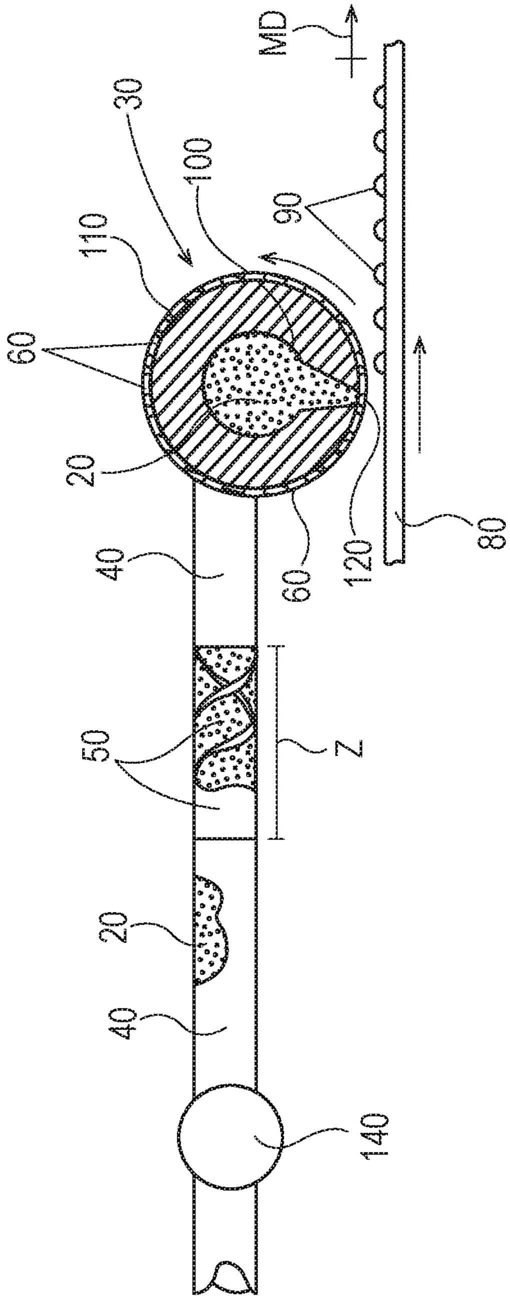
FIG. 4 is a portion of an apparatus.

The distributor 30 can be a cylinder 110 rotationally mounted about a stator 100 with the stator being in fluid communication with the feed pipe 40 and the cylinder 110 can have a periphery 120 and there can be a plurality of apertures 60 in the periphery 120, as shown in FIG. 4. So, the apparatus 1 can comprise a stator 100 in fluid communication with the feed pipe 40. The feed pipe 40 can feed the precursor material 20 to the stator 100 after the precursor material 20 has passed through the static mixer 50.

The apparatus 1 can comprise a cylinder 110 rotationally mounted about the stator 100. The stator 100 is fed precursor material through one or both ends 130 of the cylinder 110. The cylinder 110 can have a longitudinal axis L passing through the cylinder 110 about which the cylinder 110 rotates. The cylinder 110 has a periphery 120. There can be a plurality of apertures 60 in the periphery 120 of the cylinder 110.

As the cylinder 110 is driven to rotate about its longitudinal axis L, the apertures 60 can be intermittently in fluid communication with the stator 100 as the cylinder 110 rotates about the stator 100. The cylinder 110 can be considered to have a machine direction MD in a direction of movement of the periphery 120 across the stator 100 and a cross machine direction on the periphery 120 orthogonal to the machine direction MD. The stator 100 can similarly be considered to have a cross machine direction CD parallel to the longitudinal axis L. The cross machine direction of the stator 100 can be aligned with the cross machine direction of the cylinder 110. The stator 100 can have a plurality of distribution ports 120 arranged in a cross machine direction CD of the stator 100. The distribution ports 120 are portions or zones of the stator 100 supplied with precursor material 20.

In general, precursor material 20 is fed through the static mixer 50 and feed pipe 40 to the stator 100. The stator 100 distributes the precursor feed material 20 across the operating width of the cylinder 110. As the cylinder 110 rotates about its longitudinal axis, precursor material 20 is fed through the apertures 60 as the apertures 60 pass by the stator 100. A discrete mass of precursor material 20 is fed through each aperture 60 as each aperture 60 encounters the stator 100. The mass of precursor material 20 fed through each aperture 60 as each aperture 60 passes by the stator 100 can be controlled by controlling one or both of the pressure of the precursor material within the stator 100 and the rotational velocity of the cylinder 110.

Drops of the precursor material 20 are deposited on the conveyor 80 across the operating width of the cylinder 110. The conveyor 80 can be moveable in translation relative to the longitudinal axis of the cylinder 110. The velocity of the conveyor 80 can be set relative to the tangential velocity of the cylinder 110 to control the shape that the precursor material 20 has once it is deposited on the conveyor 80. The velocity of the conveyor 80 can be the about the same as the tangential velocity of the cylinder 110.

Without being bound by theory, it is believed that an intermediate mixer 55, such as the static mixer 50, can provide for a more uniform temperature of the precursor material 20 within the distributor 30 or stator 100.

At the downstream end of the intermediate mixer 55, or static mixer 50 if used, the temperature of the precursor material 20 within the feed pipe 40 across a cross section of the feed pipe 40 can vary by less than about 10° C., or less than about 5° C., or less than about 1° C., or less than about 0.5° C.

In absence of a static mixer 50, the temperature across a cross section of the feed pipe 40 may be non-uniform. The temperature of the precursor material 20 at the center line of the feed pipe 40 may be higher than the temperature of the precursor feed material 20 at the peripheral wall of the feed pipe 40. When the precursor material 20 is discharged to the distributor 30 or stator 100, the temperature of the precursor material 20 may vary at different positions within the distributor or stator 100.

Figure 5:
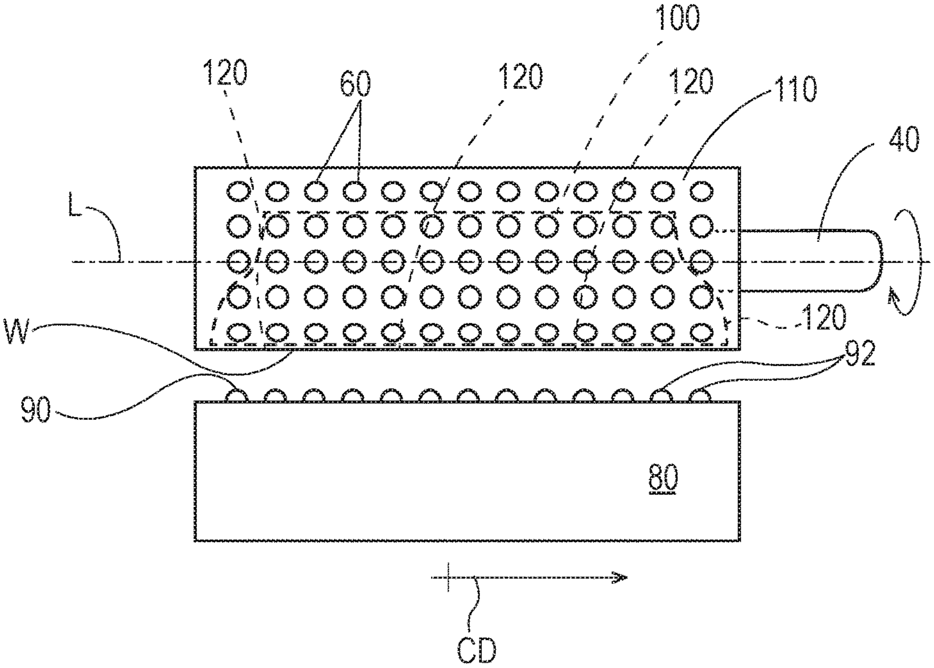
FIG. 5 is an end view an apparatus.

A view of the apparatus 1 in the machine direction MD is shown in FIG. 5. As shown in FIG. 5, the apparatus 1 can have an operating width W and the cylinder 110 can rotate about longitudinal axis L.

For a molten materials, the rheological properties of the materials tend to be temperature dependent. For instance, materials tend to have lower dynamic viscosity with increasing temperature. Since the precursor material 20 is fluid to at least a limited degree when it is deposited on the conveyor 80, the mass of precursor material 20 can deform under its own weight while resting on the conveyor 80. Rheological properties including but not limited to dynamic viscosity, kinematic viscosity, surface tension, and density can have an effect on the shape of particles 90.

Further, cohesive behavior of molten materials can vary as a function of temperature. If the temperature of the individual deposits of precursor material 20 on the conveyor differ across the cross machine direction CD of the conveyor 80, the precursor material 20 can end up forming into particles 90 having a shape that is a function of position in the cross machine direction CD of the conveyor 80. If the particles 90 formed have a variety of shapes, it can be expected that the shape of particles 90 in any given package of particles 90 will vary and that there will be variability in particle shape from one package of particles 90 to another package of particles 90.

In the realm of bulk materials that are raw materials for other products, variations in shape of the particles 90 may not be that important to the result that can be achieved with the particles. As such, it is possible that little attention has been paid to fine variations amongst the size and shape of particles 90 produced using processes described herein and variations in temperature within the distributor 30 or stator 100 may not have been recognized. In consumer products, many consumers are thought to be sensitive to the implied quality of the product that can be discerned from the consistency of the particles 90 forming the product. As such, variability of the temperature of the precursor material 20 within the distributor 30 or stator 100 is thought to be important and desired to be minimized.

Similarly, molten precursor materials 20 can be stringy. That is, depending on the temperature, the molten precursor material 20 may not release as desired from the cylinder 110. As such, the precursor material 20 deposited on the conveyor 80 may be connected to the cylinder 110 by a string of precursor material 20. Depending on how that string breaks and recoils back to the precursor material 20 deposited on the conveyor 80 and the cylinder 110, a particle 90 having a string extending there from can result. The strings may ultimately end up in the package of the particles 90 and be ground into powder during handling of the particles 90. The powder may be undesirable for a multitude of reasons including safety, handling, and aesthetics.

Without being bound by theory, it is thought that by providing for a uniform temperature across the cross section of the feed pipe 40 by employing a static mixer 40 as described herein, more uniform particles 90 can be produced as compared to an apparatus 1 that does not have a static mixer 40.

As shown in FIG. 1, flow of the precursor material 20 through the feed pipe 40 can be provided by gravity driven flow from the batch mixer 10 and the distributor 30. To provide for more controllable manufacturing, the apparatus 1 can be provided with a feed pump 140, as shown in FIG. 4. The feed pump can be in line with the feed pipe 40, with in line meaning in the line of flow of the precursor material 20. The feed pump 140 can between the batch mixer 10 and the distributor 30. If a stator 100 is employed, the feed pump 140 can be in line with the feed pipe 40, with in line meaning in the line of flow of the precursor material 20. If a stator 100 is employed, the feed pump 140 can be between the batch mixer 10 and the stator 100. In describing the position of the feed pump 140, between is used to describe the feed pump 140 being in-line downstream of the batch mixer 10 and upstream of the distributor 30 or if used, upstream of the stator 100.

The intermediate mixer 55 can be located in the distributor 30. If a static mixer 50 is employed as the intermediate mixer 55, the static mixer 50 can be within the stator 100. The feed pipe 40 can have an effective inside diameter that is the inside diameter of a pipe having the same open cross-sectional area as the average open cross-sectional area along the length of the feed pipe 40 between the intermediate mixer 55, or static mixer 50 if employed, and the distributor 30, or stator 100 if employed. The intermediate mixer 55, or static mixer 50 if employed, can be located in the distributor 30, or static mixer 50 if employed, or can be within a distance from the distributor 30, or stator 100 if employed, along the feed pipe 40 of less than about 100 effective inside diameters of the feed pipe 40. For example, If the feed pipe 40 is a pipe having a uniform 2.54 cm inside diameter, then the effective inside diameter of the feed pipe 40 is 2.54 cm. The intermediate mixer 55, or static mixer 50 if employed, can be within a distance from the distributor 30, or stator 100 if employed, along the feed pipe 40 of less than about 254 cm.

The intermediate mixer 55, or static mixer 50 if employed, can be located in the distributor 30, or static mixer 50 if employed, or can be within a distance from the distributor 30, or stator 100 if employed, along the feed pipe 40 of less than about 75 effective inside diameters of the feed pipe 40. The intermediate mixer 55, or static mixer 50 if employed, can be located in the distributor 30, or static mixer 50 if employed, or can be within a distance from the distributor 30, or stator 100 if employed, along the feed pipe 40 of less than about 50 effective inside diameters of the feed pipe 40. The intermediate mixer 55, or static mixer 50 if employed, can be located in the distributor 30, or static mixer 50 if employed, or can be within a distance from the distributor 30, or stator 100 if employed, along the feed pipe 40 of less than about 40 effective inside diameters of the feed pipe 40.

Without being bound by theory, it is thought that it is practical to provide an intermediate mixer 55, or static mixer 50 if employed, proximal the distributor 30, or stator 100 if employed, as described herein so that the variation in temperature of the precursor material 20 across a cross section of the feed pipe 40 within the feed pipe 40 is of a relatively uniform temperature across the feed pipe 40 so that the temperature of the precursor material 20 when discharged from the distributor 30, or stator 100 if employed, is relatively uniform.

The static mixer 50, if employed as an intermediate mixer 55, can be positioned in line between the feed pump 140 and the distributor 30, or if used, the stator 100. Advantageously, the static mixer 50, if employed as an intermediate mixer 55, can be upstream of the distributor 30, or if used, the stator 100.

The static mixer 50, if employed as an intermediate mixer 55, has length Z in a direction of flow in the static mixer 50. The length Z of the static mixer 50 is considered to be the amount of length that the static mixer 50 takes up in the transporting the precursor material 20 to the distributor 30 or stator 100, whichever is employed. The static mixer 50 can be a Kenics 1.905 cm inside diameter KMS 6 static mixer 50 that is 19.05 cm long and installed 91.44 cm upstream of the distributor 30 or stator 100. The feed pipe can have an inside diameter of 2.54 cm.

The static mixer 50, if employed as an intermediate mixer 55, can be within less than about 20 lengths Z of the distributor 30 or stator 100 as measured along the feed pipe 40. Without being bound by theory, it is believed that by having the static mixer 50 positioned as such that the variation in temperature across a cross section of the feed pipe 40 once the precursor material 20 reaches the distributor 30 or stator 100 can be reduced. The closer the static mixer 50 is located to the distributor 30 or stator 100, the more uniform the temperature will be across a cross section of the feed pipe 40. The static mixer 50 can be within less than about 10 lengths Z of the distributor 30 or stator 100 as measured along the feed pipe 40. The static mixer 50 can be within less than about 5 lengths Z of the distributor 30 or stator 100 as measured along the feed pipe 40.

The process for forming particles 90 can comprise the steps of: providing a precursor material 20 in a batch mixer 10 in fluid communication with a feed pipe 40; providing the precursor material 20 to the feed pipe 40; providing an intermediate mixer 55 in fluid communication with the feed pipe 40 downstream of the batch mixer 10; passing the precursor material 20 through the intermediate mixer 55; providing a stator 100 in fluid communication with the feed pipe 40; distributing the precursor material 20 to the stator 100; providing a cylinder 110 rotating about the stator 100 and rotatable about a longitudinal axis L of the cylinder 110, wherein the cylinder 110 has a periphery 120 and a plurality of apertures 60 disposed about the periphery 120; passing the precursor material 120 through the apertures 60; providing a moving conveyor 80 beneath the cylinder 110; depositing the precursor material 20 onto the moving conveyor 80; and cooling the precursor material 20 to form a plurality of particles 90. The process can be implemented using any of the apparatuses disclosed herein. The process can employ any of the precursor materials 20 disclosed herein to form any of the particles 90 disclosed herein.

The process for forming particles 90 can comprise the steps of: providing a precursor material 20 in a batch mixer 10 in fluid communication with a feed pipe 40; providing the precursor material 20 to the feed pipe 40; providing an intermediate mixer 55 in fluid communication with the feed pipe 40 downstream of the batch mixer 10; passing the precursor material 20 through the intermediate mixer 55; providing a distributor 30 having a plurality of apertures 60; transporting the precursor material 20 from the feed pipe 40 to the distributor 30; passing the precursor material 20 through the apertures 60; providing a moving conveyor 80 beneath the distributor 30; depositing the precursor material 20 on to the moving conveyor 80; and cooling the precursor material 20 to form a plurality of particles 90; wherein the precursor material 20 comprises more than about 40% by weight polyethylene glycol having a weight average molecular weight from about 2000 to about 13000 and from about 0.1% to about 20% by weight perfume. The process can be implemented using any of the apparatuses disclosed herein. The process can employ any of the precursor materials 20 disclosed herein to form any of the particles 90 disclosed herein.

The precursor material 20 can be any composition that can be processed as a molten material that can be formed into the particles 90 using the apparatus 1 and method described herein. The composition of the precursor material 20 is governed by what benefits will be provided with the particles 90. The precursor material 20 can be a raw material composition, industrial composition, consumer composition, or any other composition that can advantageously be provided in a particulate form.

The precursor material 20 can be a fabric treatment composition. The precursor material 20, and thereby the particles 90, can comprise more than about 40% by weight polyethylene glycol having a weight average molecular weight from about 2000 to about 13000. Polyethylene glycol (PEG) has a relatively low cost, may be formed into many different shapes and sizes, minimizes unencapsulated perfume diffusion, and dissolves well in water. PEG comes in various weight average molecular weights. A suitable weight average molecular weight range of PEG includes from about 2,000 to about 13,000, from about 4,000 to about 12,000, alternatively from about 5,000 to about 11,000, alternatively from about 6,000 to about 10,000, alternatively from about 7,000 to about 9,000, alternatively combinations thereof. PEG is available from BASF, for example PLURIOL E 8000.

The precursor material 20, and thereby the particles 90, can comprise more than about 40% by weight of the particles of PEG. The precursor material 20, and thereby the particles 90, can comprise more than about 50% by weight of the particles of PEG. The precursor material 20, and thereby the particles 90, can comprise more than about 60% by weight of the particles of PEG. The precursor material 20, and thereby the particles 90, may comprise from about 65% to about 99% by weight of the composition of PEG. The precursor material 20, and thereby the particles 90, may comprise from about 40% to about 99% by weight of the composition of PEG.

Alternatively, the precursor material 20, and thereby the particles 90, can comprise from about 40% to less than about 90%, alternatively from about 45% to about 75%, alternatively from about 50% to about 70%, alternatively combinations thereof and any whole percentages or ranges of whole percentages within any of the aforementioned ranges, of PEG by weight of the precursor material 20, and thereby the particles 90.

Depending on the application, the precursor material 20, and thereby the particles 90, can comprise from about 0.5% to about 5% by weight of the particles of a balancing agent selected from the group consisting of glycerin, polypropylene glycol, isopropyl myristate, dipropylene glycol, 1,2 propanediol, PEG having a weight average molecular weight less than 2,000, and mixtures thereof.

In addition to the PEG in the precursor material 20, and thereby the particles 90, the precursor material 20, and thereby the particles 90, can further comprise 0.1% to about 20% by weight perfume. The perfume can be unencapsulated perfume, encapsulated perfume, perfume provided by a perfume delivery technology, or a perfume provided in some other manner. Perfumes are generally described in U.S. Pat. No. 7,186,680 at column 10, line 56, to column 25, line 22. The precursor material 20, and thereby particles 90, can comprise unencapsulated perfume and are essentially free of perfume carriers, such as a perfume microcapsules. The precursor material 20, and there by particles 90, can comprise perfume carrier materials (and perfume contained therein). Examples of perfume carrier materials are described in U.S. Pat. No. 7,186,680, column 25, line 23, to column 31, line 7. Specific examples of perfume carrier materials may include cyclodextrin and zeolites.

The precursor material 20, and thereby particles 90, can comprise about 0.1% to about 20%, alternatively about 1% to about 15%, alternatively 2% to about 10%, alternatively combinations thereof and any whole percentages within any of the aforementioned ranges, of perfume by weight of the precursor material 20 or particles 90. The perfume can be unencapsulated perfume and or encapsulated perfume.

The precursor material 20, and thereby particles 90, can be free or essentially free of a perfume carrier. The precursor material 20, and thereby particles 90, may comprise about 0.1% to about 20%, alternatively about 1% to about 15%, alternatively 2% to about 10%, alternatively combinations thereof and any whole percentages within any of the aforementioned ranges, of unencapsulated perfume by weight of the precursor material 20, and thereby particles 90.

The precursor material 20, and thereby particles 90, can comprise unencapsulated perfume and perfume microcapsules. The precursor material 20, and thereby particles 90, may comprise about 0.1% to about 20%, alternatively about 1% to about 15%, alternatively from about 2% to about 10%, alternatively combinations thereof and any whole percentages or ranges of whole percentages within any of the aforementioned ranges, of the unencapsulated perfume by weight of the precursor material 20, and thereby particles 90. Such levels of unencapsulated perfume can be appropriate for any of the precursor materials 20, and thereby particles 90, disclosed herein that have unencapsulated perfume.

The precursor material 20, and thereby particles 90, can comprise unencapsulated perfume and a perfume microcapsule but be free or essentially free of other perfume carriers. The precursor material 20, and thereby particles 90, can comprise unencapsulated perfume and perfume microcapsules and be free of other perfume carriers.

The precursor material 20, and thereby particles 90, can comprise encapsulated perfume. Encapsulated perfume can be provided as plurality of perfume microcapsules. A perfume microcapsule is perfume oil enclosed within a shell. The shell can have an average shell thickness less than the maximum dimension of the perfume core. The perfume microcapsules can be friable perfume microcapsules. The perfume microcapsules can be moisture activated perfume microcapsules.

The perfume microcapsules can comprise a melamine/formaldehyde shell. Perfume microcapsules may be obtained from Appleton, Quest International, or International Flavor & Fragrances, or other suitable source. The perfume microcapsule shell can be coated with polymer to enhance the ability of the perfume microcapsule to adhere to fabric. This can be desirable if the particles 90 are designed to be a fabric treatment composition. The perfume microcapsules can be those described in U.S. Patent Pub. 2008/0305982.

The precursor material 20, and thereby particles 90, can comprise about 0.1% to about 20%, alternatively about 1% to about 15%, alternatively 2% to about 10%, alternatively combinations thereof and any whole percentages within any of the aforementioned ranges, of encapsulated perfume by weight of the precursor material 20, or particles 90.

The precursor material 20, and thereby particles 90, can comprise perfume microcapsules but be free of or essentially free of unencapsulated perfume. The precursor material 20, and thereby particles 90, may comprise about 0.1% to about 20%, alternatively about 1% to about 15%, alternatively about 2% to about 10%, alternatively combinations thereof and any whole percentages within any of the aforementioned ranges, of encapsulated perfume by weight of the precursor material 20 or particles 90.

The precursor material 20 can be prepared by providing molten PEG into the batch mixer 10. The batch mixer 10 can be heated so as to help prepare the precursor material 20 at the desired temperature. Perfume is added to the molten PEG. Dye, if present, can be added to the batch mixer 10. Other adjunct materials can be added to the precursor material 20 if desired. If dye is employed, the precursor material 20 and particles 90 may comprise dye. The precursor material 20, and thereby particles 90, may comprise less than about 0.1%, alternatively about 0.001% to about 0.1%, alternatively about 0.01% to about 0.02%, alternatively combinations thereof and any hundredths of percent or ranges of hundredths of percent within any of the aforementioned ranges, of dye by weight of the precursor material 20 or particles 90. Examples of suitable dyes include, but are not limited to, LIQUITINT PINK AM, AQUA AS CYAN 15, and VIOLET FL, available from Milliken Chemical.

The particles 90 may have a variety of shapes. The particles 90 may be formed into different shapes include tablets, pills, spheres, and the like. A particle 90 can have a shape selected from the group consisting of spherical, hemispherical, compressed hemispherical, lentil shaped, and oblong. Lentil shaped refers to the shape of a lentil bean. Compressed hemispherical refers to a shape corresponding to a hemisphere that is at least partially flattened such that the curvature of the curved surface is less, on average, than the curvature of a hemisphere having the same radius. A compressed hemispherical particle 90 can have a ratio of height to maximum based dimension of from about 0.01 to about 0.4, alternatively from about 0.1 to about 0.4, alternatively from about 0.2 to about 0.3. Oblong shaped refers to a shape having a maximum dimension and a maximum secondary dimension orthogonal to the maximum dimension, wherein the ratio of maximum dimension to the maximum secondary dimension is greater than about 1.2. An oblong shape can have a ratio of maximum base dimension to maximum minor base dimension greater than about 1.5. An oblong shape can have a ratio of maximum base dimension to maximum minor base dimension greater than about 2. Oblong shaped particles can have a maximum base dimension from about 2 mm to about 6 mm, a maximum minor base dimension of from about 2 mm to about 6 mm.

Individual particles 90 can have a mass from about 0.1 mg to about 5 g, alternatively from about 10 mg to about 1 g, alternatively from about 10 mg to about 500 mg, alternatively from about 10 mg to about 250 mg, alternatively from about 0.95 mg to about 125 mg, alternatively combinations thereof and any whole numbers or ranges of whole numbers of mg within any of the aforementioned ranges. In a plurality of particles 90, individual particles can have a shape selected from the group consisting of spherical, hemispherical, compressed hemispherical, lentil shaped, and oblong.

An individual particle may have a volume from about 0.003 $cm^3$ to about 0.15 $cm^3$. A number of particles 90 may collectively comprise a dose for dosing to a laundry washing machine or laundry wash basin. A single dose of the particles 90 may comprise from about 1 g to about 27 g. A single dose of the particles 90 may comprise from about 5 g to about 27 g, alternatively from about 13 g to about 27 g, alternatively from about 14 g to about 20 g, alternatively from about 15 g to about 19 g, alternatively from about 18 g to about 19 g, alternatively combinations thereof and any whole numbers of grams or ranges of whole numbers of grams within any of the aforementioned ranges. The individual particles 90 forming the dose of particles 90 that can make up the dose can have a mass from about 0.95 mg to about 2 g. The plurality of particles 90 can be made up of particles having different size, shape, and/or mass. The particles 90 in a dose can have a maximum dimension less than about 1 centimeter.

Figure 6:
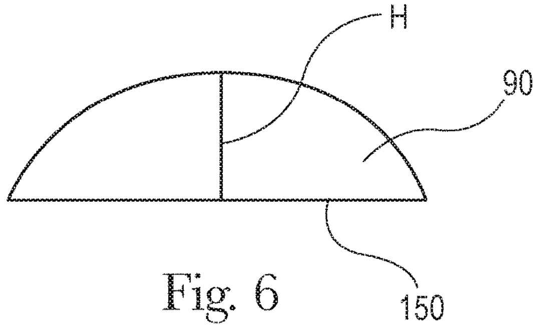
FIG. 6 is a profile view of a particle.

A particle 90 that can be manufactured as provided herein is shown in FIG. 6. FIG. 6 is a profile view of a single particle 90. The particle 90 can have a substantially flat base 150 and a height H. The height H of a particle 90 is measured as the maximum extent of the particle 90 in a direction orthogonal to the substantially flat base 150. The height H can be measured conveniently using image analysis software to analyze a profile view of the particle 90.

Figure 7:
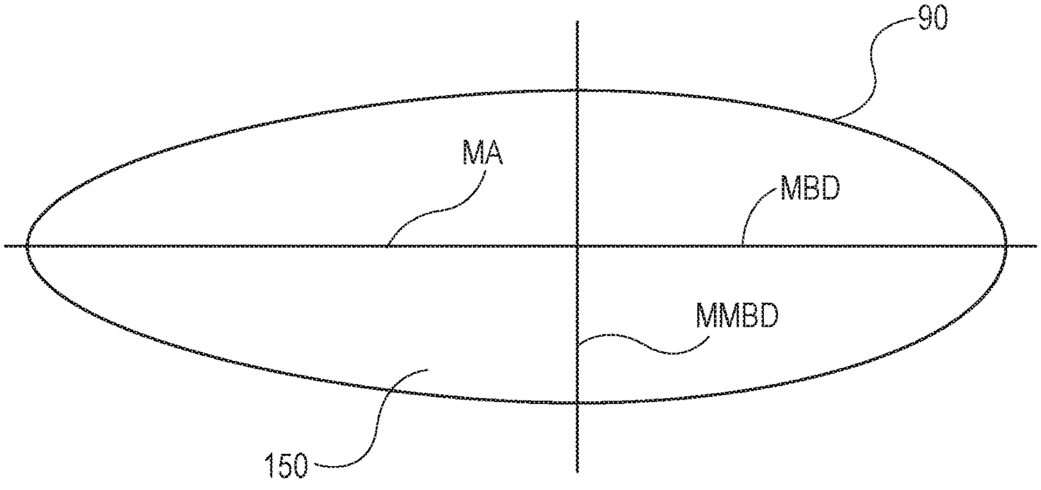
FIG. 7 is a bottom view of a particle.

A bottom view of the particle 90 that can be manufactured as provided herein is shown in FIG. 7. The base 150 can have a maximum base dimension MBD. The maximum base dimension MBD is the length of the maximum extent of the base 150 in the plane of the base 150. If the base 150 has the shape of an ellipse, the maximum base dimension MBD is the length of the major axis of the ellipse.

The particles 90 can be considered to have a major axis MA in line with the maximum base dimension MBD. The base 150 can further have a maximum minor base dimension MMBD. The maximum minor base dimension MMBD is measured orthogonal to the major axis MA and in plane with the base 150.

Figure 8:
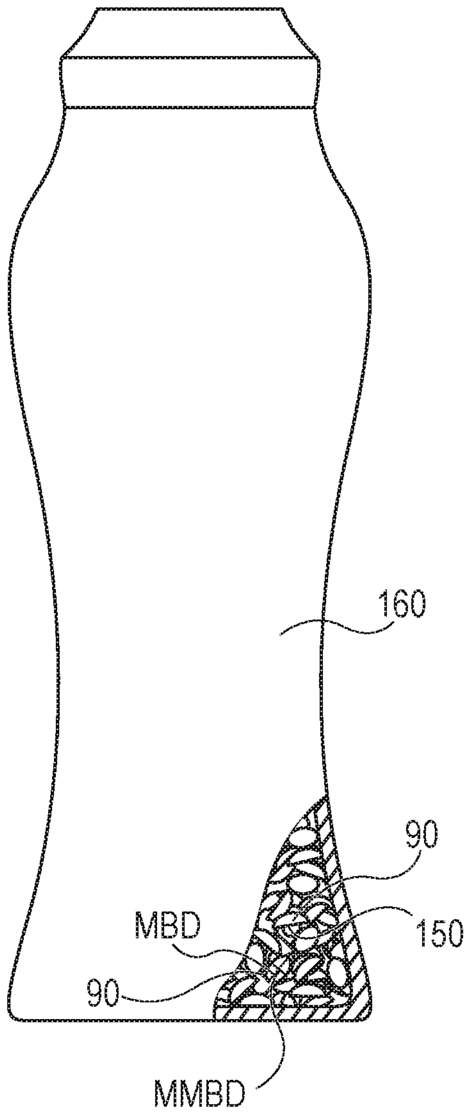
FIG. 8 is a packaged composition.

A packaged composition 160 comprising a plurality of particles 90 in a package 160 is shown in FIG. 8. Substantially all of the particles 90 in the package 160 can have a substantially flat base 150 and a height H measured orthogonal to the base 150 and together the particles 90 can have distribution of heights H, wherein the distribution of heights H has a mean height between about 1 mm and about 5 mm and a height H standard deviation of less than about 0.3. More than about 90%, or even more than about 95%, or even more than about 99% of the particles 90 in the package 160 can have a substantially flat base 150 and a height H measured orthogonal to the base 150 and together the particles 90 can have distribution of heights H, wherein the distribution of heights H has a mean height between about 1 mm and about 5 mm and a height H standard deviation of less than about 0.3 or even less than about 0.2 or even less than about 0.15 or even less than about 0.13, any combinations of the fractions of particles 90 in the package having a substantially flat base 150 as set forth herein and the height H standard deviations set forth herein being contemplated. For example, more than about 95% of the particles 90 in the package 160 can have a substantially flat base 150 and a height H measured orthogonal to the base 150 and together the particles 90 can have distribution of heights H, wherein the distribution of heights H has a mean height between about 1 mm and about 5 mm and a height H standard deviation of less than about 0.15. Packages 160 containing particles 90 as described herein are thought to provide for relatively uniform fill heights amongst different packages 160 having substantially the same filled weight.

Substantially all of the particles 90 in the package 160 can have a substantially flat base 150 and a maximum base dimension MBD and the particles 90 together can have a distribution of maximum base dimensions MBD wherein the distribution of maximum base dimensions MBD can have a mean maximum base dimension MBD between about 2 mm and about 7 mm and a maximum base dimension MBD standard deviation less than about 0.5. Packages 160 containing particles 90 as such are thought to provide for relatively uniform fill heights amongst different packages 160 having substantially the same filled weight. Substantially all of the particles 90 in the package 160 can have a substantially flat base 150 and a maximum base dimension MBD and the particles 90 together can have a distribution of maximum base dimensions MBD wherein the distribution of maximum base dimensions MBD can have a mean maximum base dimension MBD between about 2 mm and about 7 mm and a maximum base dimension MBD standard deviation less than about 0.3 or even less than about 0.25.

Substantially all of the particles 90 in the package 160 can have a substantially flat base 150 and have a major axis MA in line with the maximum base dimension MBD and maximum minor base dimension MMBD measured orthogonal to the major axis MA and in plane with the base 150. Together such particles 90 can have a distribution of maximum minor base dimensions MMBD wherein the distribution of maximum minor base dimensions MMBD has a mean maximum minor base dimension MMBD standard deviation less than about 0.5 or even less than about 0.3 or even less than about 0.25. Packages 160 containing particles 90 as such are thought to provide for relatively uniform fill heights amongst different packages 160 having approximately the same filled weight.

Particles 90 having one or more of a tight distribution of heights H, maximum base dimension MBD, and or maximum minor base dimensions MMBD, as disclosed herein, are thought to provide for packages 160 containing particles 90 that have relatively uniform fill heights amongst different packages 160 having substantially the same filled weight. For example, substantially all of the particles 90 in the package 160 can have a substantially flat base 150 and a height H measured orthogonal to the base 150 and together the particles 90 can have distribution of heights H, wherein the distribution of heights H has a mean height between about 1 mm and about 5 mm and a height H standard deviation of less than about 0.3 and substantially all of the particles 90 in the package 160 can have a substantially flat base 150 and a maximum base dimension MBD and the particles 90 together can have a distribution of maximum base dimensions MBD wherein the distribution of maximum base dimensions MBD can have a mean maximum base dimension MBD between about 2 mm and about 7 mm and a maximum base dimension MBD standard deviation less than about 0.5.

Substantially all or more than about 90% by weight or more than 95% by weight or more than 99% by weight can have a height H wherein the distribution of heights H has a mean height between about 1 mm and about 5 mm and a height H standard deviation of less than about 0.3 or less than about 0.2 or less than about 0.15 or less than about 0.13, a maximum base dimension MBD wherein the distribution of maximum base dimensions MBD has a mean maximum base dimension MBD between about 2 mm and about 7 mm and a maximum base dimension MBD standard deviation less than about 0.5 or less than about 0.3 or less than about 0.25, a maximum minor base dimension MMBD wherein the distribution of maximum minor base dimensions MMBD has a mean maximum minor base dimension MMBD between about 2 mm and about 7 mm and a maximum minor base dimension MMBD standard deviation less than about 0.5 or less than about 0.3 or less than about 0.25. Any combinations of the aforesaid ranges, and ranges within such ranges, for each property and other ranges disclosed herein for such properties being contemplated.

Optionally, substantially all of the particles 90 in the package 160 can have a substantially flat base 150 and a height H measured orthogonal to the base 150 and together the particles 90 can have a distribution of heights H, wherein the distribution of heights H has a mean height between about 1 mm and about 5 mm and a height H standard deviation of less than about 0.3 and substantially all of the particles 90 in the package 160 can have a substantially flat base 150 and a maximum base dimension MBD and the particles 90 together can have a distribution of maximum base dimensions MBD wherein the distribution of maximum base dimensions MBD can have a mean maximum base dimension MBD between about 2 mm and about 7 mm and a maximum base dimension MBD standard deviation less than about 0.5 and substantially all of the particles 90 in the package 160 can have a substantially flat base 150 and have a major axis MA in line with the maximum base dimension MBD and maximum minor base dimension MMBD measured orthogonal to the major axis MA and in plane with the base 150 wherein the distribution of maximum minor base dimensions MMBD has a mean maximum minor base dimension MMBD between about 2 mm and about 7 mm and a maximum minor base dimension MMBD standard deviation less than about 0.5 or less than about 0.3 or less than about 0.25.

To evaluate the efficacy of the static mixer 50 for improving the ability to make uniformly shaped particles 90, a comparison was made between production runs made with and without a static mixer 50.

A 50 kg batch of precursor material 20 was prepared in a mixer. Molten PEG8000 was added to a jacketed mixer held at 70° C. and agitated with a pitch blade agitator at 125 rpm. Butylated hydroxytoluene was added to the mixer at a level of 0.01% by weight of the precursor material 20. Dipropylene glycol was added to the mixer at a level of 1.08% by weight of the precursor material 20. A water based slurry of perfume microcapsules was added to the mixer at a level of 4.04% by weight of the precursor material 20. Unencapsulated perfume was added to the mixer at a level of 7.50% by weight of the precursor material 20. Dye was added to the mixer at a level of 0.0095% by weight of the precursor material 20. The PEG accounted for 87.36% by weight of the precursor material 20. The precursor material 20 was mixed for 30 minutes.

The precursor material 20 was formed into particles 90 on a Sandvik Rotoform 3000 having a 750 mm wide 10 m long belt. The cylinder 110 had 2 mm diameter apertures 60 set at a 10 mm pitch in the cross machine direction CD and 9.35 mm pitch in the machine direction MD. The cylinder was set at approximately 3 mm above the belt. The belt speed and rotational speed of the cylinder 110 was set at 10 m/min.

After mixing the precursor material 20, the precursor material 20 was pumped at a constant 3.1 kg/min rate from the mixer 10 through a plate and frame heat exchanger set to control the outlet temperature to 50° C.

Figure 9:
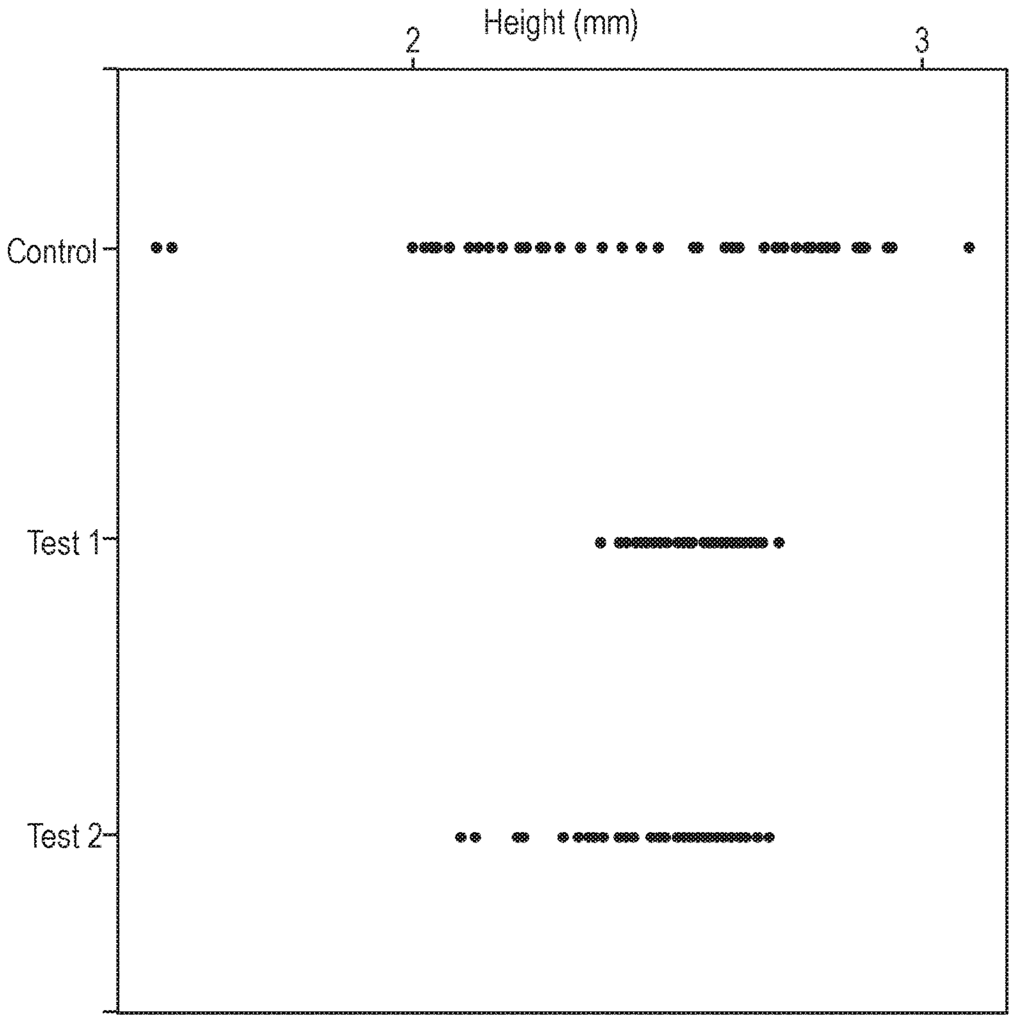
FIG. 9 is a graph of the distribution of heights of particles made with and without use of an static mixer.
Figure 10:
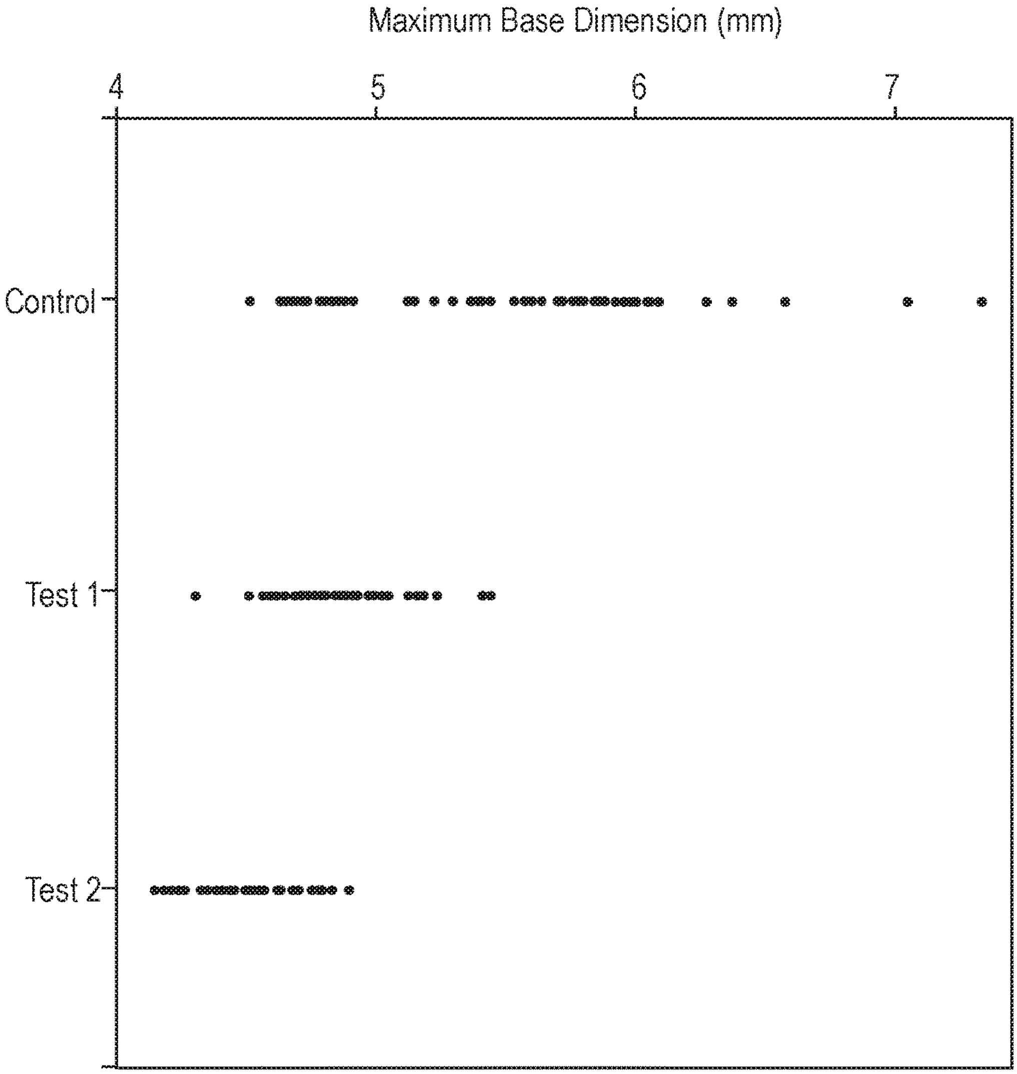
FIG. 10 is a graph of the distribution of maximum base dimensions of particles made with and without use of a static mixer.
Figure 11:
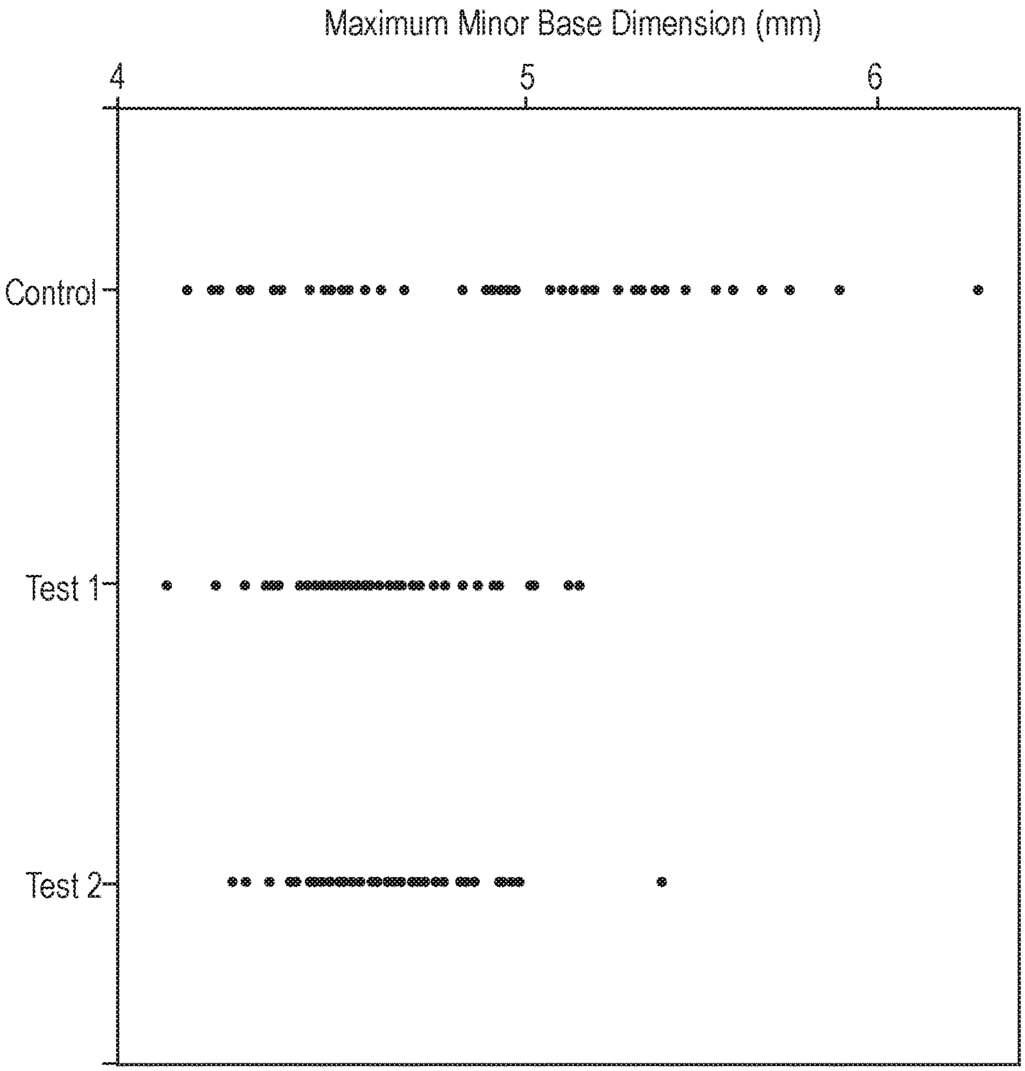
FIG. 11 is a graph of the distribution of maximum minor base dimensions of particles made with and without use of a static mixer.

A control run in absence of the static mixer 50 was performed. Sixty particles 90 were obtained from a portion of the control run. Graphs of the distributions of the height H, maximum base dimension MBD, and maximum minor base dimension MMBD for the control run are shown in FIGS. 9, 10, and 11, and labeled as “Control.”

Test runs were performed with a Kenics 1.905 cm KMS 6 static mixer 50 installed 91.44 cm upstream of the stator. For each test run, particles 90 were obtained from a portion of the test run. Graphs of the distributions of the height H, maximum base dimension MBD, and maximum minor base dimension MMBD obtained with the static mixer 50 installed are shown in FIGS. 9, 10, and 11, and labeled as “Test 1” and “Test 2.”

Table 1 is a summary of results of the comparison.

TABLE 1

Comparison of productions runs with and without a static mixer (measurements of minimum, maximum, and mean are in mm).

| | H | MBD | MMBD |
|---|---|---|---|
| | | Control | n = 60 |
| Minimum (mm) | 1.50 | 4.47 | 4.05 |
| Maximum (mm) | 3.09 | 7.29 | 6.30 |
| Mean (mm) | 2.44 | 5.43 | 4.88 |
| Standard Deviation | 0.35 | 0.63 | 0.52 |
| | | Test 1 | n = 58 |
| Minimum (mm) | 2.37 | 4.27 | 4.00 |
| Maximum (mm) | 2.72 | 5.41 | 5.17 |
| Mean (mm) | 2.54 | 4.79 | 4.57 |
| Standard Deviation | 0.08 | 0.22 | 0.22 |
| | | Test 2 | n = 60 |
| Minimum (mm) | 2.10 | 4.13 | 4.19 |
| Maximum (mm) | 2.70 | 4.87 | 5.41 |
| Mean (mm) | 2.49 | 4.42 | 4.62 |
| Standard Deviation | 0.13 | 0.17 | 0.22 |

As shown in FIGS. 9, 10, and 11, including a static mixer 50 in line between the feed pump 140 and stator 100 tends to tighten the distribution of height H, maximum base dimension MBD, and maximum minor base dimension MMBD. Tightening of these distributions is reflected in the standard deviation for each of the distributions, each of which is lower when a static mixer 50 is employed as compared when no static mixer 50 is employed. Tighter distributions are associated with more uniform particles 90. For each of measured properties for which distributions were generated, the p-value as determined by an F-test was less than 0.001.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as “40 mm” is intended to mean “about 40 mm.”

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A packaged composition comprising a plurality of particles in a package, wherein said particles comprise:

more than about 40% by weight of said particles of polyethylene glycol, wherein said polyethylene glycol has a weight average molecular weight from about 5000 to about 11000; and from about 0.1% to about 20% by weight of said particles of perfume;

wherein substantially all of said particles in said package have a substantially flat base and a height measured orthogonal to said base and together said particles have a distribution of heights, wherein said distribution of heights has a mean height between about 1 mm and about 5 mm and a height standard deviation less than about 0.3.

2. The packaged composition according to claim 1, wherein substantially all of said particles in said package have a substantially flat base and a maximum base dimension and said particles together have a distribution of maximum base dimensions wherein said distribution of maximum base dimensions has a mean maximum base dimension between about 2 mm and about 7 mm and a maximum base dimension standard deviation less than about 0.5.

3. The packaged composition according to claim 2, wherein substantially all of said particles in said package have a substantially flat base and have a major axis in line with said maximum base dimension and a maximum minor base dimension measured orthogonal to said major axis and in plane with said base and together said particles have a distribution of maximum minor base dimensions wherein said distribution of maximum minor base dimensions has a mean maximum minor base dimension between about 2 mm and about 7 mm and a maximum minor base dimension standard deviation less than about 0.5.

4. The package composition according to claim 1, wherein said perfume comprises encapsulated perfume.

5. The packaged composition according to claim 4, wherein said particles comprises between about 0.1% and about 20% by weight encapsulated perfume.

6. The packaged composition according to claim 1, wherein said perfume comprises encapsulated perfume and unencapsulated perfume.

7. The packaged composition according to claim 1, wherein said particles have an individual mass between about 0.1 mg to about 5 g.

8. The packaged composition according to claim 1, wherein more than about 90% of said particles in said package have a substantially flat base and a height measured orthogonal to said base and together said particles have a distribution of heights, wherein said distribution of heights has a mean height between about 1 mm and about 5 mm and a height standard deviation less than about 0.3.

9. The packaged composition according to claim 1, wherein more than about 90% of said particles in said package have a substantially flat base and a height measured orthogonal to said base and together said particles have a distribution of heights, wherein said distribution of heights has a mean height between about 1 mm and about 5 mm and a height standard deviation less than about 0.2.

10. The packaged composition according to claim 9, wherein said particles have an individual mass between about 0.1 mg to about 5 g.

11. The package composition according to claim 10, wherein said perfume comprises encapsulated perfume.

12. The packaged composition according to claim 11, wherein said particles comprises between about 0.1% and about 20% by weight encapsulated perfume.

13. The packaged composition according to claim 12, wherein said perfume comprises encapsulated perfume and unencapsulated perfume.

14. The packaged composition according to claim 1, wherein more than about 90% of said particles in said package have a substantially flat base and a height measured orthogonal to said base and together said particles have a distribution of heights, wherein said distribution of heights has a mean height between about 1 mm and about 5 mm and a height standard deviation less than about 0.15.

15. The packaged composition according to claim 14, wherein said particles comprises between about 0.1% and about 20% by weight encapsulated perfume.

16. The packaged composition according to claim 1, wherein more than about 95% of said particles in said package have a substantially flat base and a height measured orthogonal to said base and together said particles have a distribution of heights, wherein said distribution of heights has a mean height between about 1 mm and about 5 mm and a height standard deviation less than about 0.3.

17. The packaged composition according to claim 16, wherein said particles have an individual mass between about 0.1 mg to about 5 g.

18. The packaged composition according to claim 17, wherein said perfume comprises encapsulated perfume.

19. The packaged composition according to claim 1, wherein more than about 99% of said particles in said package have a substantially flat base and a height measured orthogonal to said base and together said particles have a distribution of heights, wherein said distribution of heights has a mean height between about 1 mm and about 5 mm and a height standard deviation less than about 0.3.

20. The packaged composition according to claim 19, wherein said particles comprises between about 0.1% and about 20% by weight encapsulated perfume.

* * * * *